United States Patent
Li

(10) Patent No.: US 11,357,583 B2
(45) Date of Patent: Jun. 14, 2022

(54) LAPAROSCOPE-HOLDING ROBOT SYSTEM FOR LAPAROSCOPIC SURGERY

(71) Applicant: CHENGDU BORNS MEDICAL ROBOTICS INC., Sichuan (CN)

(72) Inventor: Zhiqiang Li, Sichuan (CN)

(73) Assignee: CHENGDU BORNS MEDICAL ROBOTICS INC., Sichuan (CN)

( * ) Notice: Subject to any disclaimer, the term of this patent is extended or adjusted under 35 U.S.C. 154(b) by 0 days.

(21) Appl. No.: 17/045,108

(22) PCT Filed: Jul. 27, 2018

(86) PCT No.: PCT/CN2018/097541
§ 371 (c)(1),
(2) Date: Oct. 2, 2020

(87) PCT Pub. No.: WO2019/200773
PCT Pub. Date: Oct. 24, 2019

(65) Prior Publication Data
US 2021/0145527 A1 May 20, 2021

(30) Foreign Application Priority Data

Apr. 17, 2018 (CN) .......................... 201810343711.7
Apr. 17, 2018 (CN) .......................... 201810345131.1

(51) Int. Cl.
*A61B 34/37* (2016.01)
*A61B 34/30* (2016.01)
(Continued)

(52) U.S. Cl.
CPC .......... *A61B 34/30* (2016.02); *A61B 1/00128* (2013.01); *A61B 1/00149* (2013.01);
(Continued)

(58) Field of Classification Search
CPC ... A61B 34/30; A61B 17/00234; A61B 50/13; A61B 1/00128; A61B 1/00149;
(Continued)

(56) References Cited

U.S. PATENT DOCUMENTS

| 7,822,466 B2 | 10/2010 | Stoianovici et al. |
| 2002/0082612 A1* | 6/2002 | Moll .................. A61B 34/30 606/130 |

(Continued)

FOREIGN PATENT DOCUMENTS

| CN | 203752148 U | 8/2014 |
| CN | 105188590 A | 12/2015 |

(Continued)

OTHER PUBLICATIONS

International Search Report (Translation) for International Patent Application No. PCT/CN2018/097541, dated Dec. 18, 2018, 2 pages.

(Continued)

*Primary Examiner* — Richard G Louis
(74) *Attorney, Agent, or Firm* — Ulmer & Berne LLP

(57) ABSTRACT

Provided is a laparoscope-holding robot system for laparoscopic surgery, which belongs to the technical field of robot control and is used to solve the technical problem in the prior art of the operations of a laparoscope-holding robot for laparoscopic surgery being inflexible and same further requiring a doctor to assist in operations. The laparoscope-holding robot system for laparoscopic surgery of the present invention comprises a trolley rack, a surgical tool and a mechanical arm. Since the mechanical arm has at least six degrees of freedom, the mechanical arm can completely simulate the range of motion of a human arm and is no different from the human arm in terms of flexibility, so as to precisely locate the position of a lesion that actually needs (Continued)

to be operated without requiring a doctor to assist in operations.

22 Claims, 10 Drawing Sheets

(51) Int. Cl.
    *A61B 50/13* (2016.01)
    *A61B 1/00* (2006.01)
    *A61B 1/313* (2006.01)
    *A61B 17/00* (2006.01)
    *B25J 18/00* (2006.01)

(52) U.S. Cl.
    CPC ...... *A61B 1/3132* (2013.01); *A61B 17/00234* (2013.01); *A61B 50/13* (2016.02); *B25J 18/00* (2013.01); *A61B 2034/301* (2016.02); *A61B 2034/302* (2016.02)

(58) Field of Classification Search
    CPC ............ A61B 1/3132; A61B 2034/301; A61B 2034/302; A61B 2017/00477; A61B 34/35; B25J 18/00
    See application file for complete search history.

(56) References Cited

U.S. PATENT DOCUMENTS

| | | | |
|---|---|---|---|
| 2007/0089557 A1 | 4/2007 | Solomon et al. | |
| 2007/0156285 A1 | 7/2007 | Sillman et al. | |
| 2010/0069920 A1* | 3/2010 | Naylor | A61B 34/30 606/130 |
| 2010/0204713 A1 | 8/2010 | Ruiz Morales | |
| 2010/0225209 A1 | 9/2010 | Goldberg et al. | |
| 2011/0277776 A1* | 11/2011 | McGrogan | A61B 34/00 128/852 |
| 2013/0085389 A1* | 4/2013 | Tsang | A61B 8/12 600/442 |
| 2016/0001038 A1 | 1/2016 | Romo et al. | |
| 2017/0079722 A1 | 3/2017 | O'Grady et al. | |
| 2017/0273748 A1 | 9/2017 | Hourtash et al. | |
| 2017/0333141 A1 | 11/2017 | Itkowitz et al. | |
| 2017/0333142 A1 | 11/2017 | Itkowitz et al. | |
| 2018/0280095 A1* | 10/2018 | Lattimore | A61B 50/13 |

FOREIGN PATENT DOCUMENTS

| | | | |
|---|---|---|---|
| CN | 105816243 A | | 8/2016 |
| CN | 105832488 A | | 8/2016 |
| CN | 107260308 A | * | 10/2017 |
| CN | 107361849 A | | 11/2017 |
| CN | 206880734 U | * | 1/2018 |
| CN | 206880734 U | | 1/2018 |
| WO | 2017220822 A1 | | 12/2017 |

OTHER PUBLICATIONS

International Search Report, Written Opinion, and Claims (Translation) for PCT International App. Serial No. PCT/CN2018/097467; dated Oct. 8, 2018; 9 pages.

Supplementary European Search Report of the European Patent Office, Issued in European Application No. 18915439.6-1113; dated Jan. 4, 2022; 8 pages.

* cited by examiner

LAPAROSCOPE-HOLDING ROBOT SYSTEM FOR LAPAROSCOPIC SURGERY

CROSS-REFERENCE TO RELATED APPLICATIONS

This application is a United States national stage entry under 35 U.S.C. § 371 of international patent application number PCT/CN2018/097541, filed Jul. 27, 2018, which claims the priority benefit of Chinese patent application CN201810345131.1 filed on Apr. 17, 2018, titled "Laparoscope-holding Robot System for Laparoscopic Surgery", and the priority benefit of Chinese patent application CN201810343711.7 filed on Apr. 17, 2018, titled "Laparoscope-holding Robot System for Laparoscopic Surgery", each of which is incorporated by reference herein in their respective entireties.

TECHNICAL FIELD

The present disclosure relates to the technical field of robot control, in particular to a laparoscope-holding robot system for laparoscopic surgery.

BACKGROUND

Minimally invasive surgery has many advantages, such as rapid postoperative recovery and small trauma, on the basis of conventional surgeries, and is practiced and rapidly developed. As a representative of minimally invasive surgery, the laparoscopic minimally invasive surgery has become a significant revolution for conventional open operations. With the extension of the minimally invasive surgical field, the minimally invasive surgical robot system provides a new approach for further perfecting the minimally invasive surgery against the limitations of conventional laparoscopic technology in clinical applications.

A common laparoscope-holding robot for laparoscopic surgery has certain shortcomings in operation space and movement mode, and the endoscope position also needs to be adjusted by a doctor through manual operation, in particular, the accuracy of execution of complex actions is not high enough, and a relatively ideal degree of automation and intelligence cannot be achieved.

SUMMARY

The present disclosure provides a laparoscope-holding robot system for laparoscopic surgery, for solving the technical problem in the prior art that the laparoscope-holding robot for laparoscopic surgery is inflexible in operation and also requires a doctor to assist in operation.

The present disclosure provides a laparoscope-holding robot system for laparoscopic surgery, including a trolley rack, a surgical tool and a mechanical arm provided on the trolley rack, wherein the surgical tool is fixed to a front end of the mechanical arm, wherein the mechanical arm has at least six degrees of freedom.

In one embodiment, the mechanical arm includes a terminal joint and an intermediate joint respectively connected to a first connecting arm and a second connecting arm, and the terminal joint includes a first joint connected to the trolley rack and a sixth joint connected to a mounting seat of the surgical tool.

In one embodiment, the intermediate joint includes a second joint rotationally connected to the first joint, a third joint connecting the first connecting arm and the second connecting arm, a fourth joint rotationally connected to the second connecting arm and a fifth joint rotationally connected to the fourth joint and the sixth joint, respectively.

In one embodiment, when the second connecting arm rotates with an axis of the third joint as a rotation axis, a maximum rotation angle is 360°.

In one embodiment, when the first connecting arm rotates with an axis of the second joint as a rotation axis, a maximum rotation angle is 180°.

In one embodiment, the trolley rack includes a base and a post fixedly provided on the base, and the mechanical arm is provided on the post.

In one embodiment, an adapter flange is provided on a side surface of the post, and the mechanical arm is fixedly connected to the adapter flange.

In one embodiment, a top end of the post is provided with a mechanical interface, and the mechanical arm is fixedly connected to the mechanical interface.

In one embodiment, a wire pipe is provided on the first joint at a position connected to the trolley rack, and an axial direction of the wire pipe is perpendicular to an axial direction of the first joint and a height direction of the post, respectively.

In one embodiment, the bottom of the base is provided with two directional casters and two universal casters having a braking function, respectively.

The present disclosure further provides a laparoscope-holding robot system for laparoscopic surgery, including a trolley rack, a surgical tool and a mechanical arm provided on the trolley rack, wherein a front end of the mechanical arm is provided with an extension plate having a quick-release device, and the surgical tool is fixed on the extension plate by the quick-release device, wherein the mechanical arm has at least six degrees of freedom.

In one embodiment, the mechanical arm includes a terminal joint and an intermediate joint respectively connected to a first connecting arm and a second connecting arm, and the terminal joint includes a first joint connected to the trolley rack and a sixth joint connected to a mounting seat of the surgical tool.

In one embodiment, the intermediate joint includes a second joint rotationally connected to the first joint, a third joint connecting the first connecting arm and the second connecting arm, a fourth joint rotationally connected to the second connecting arm and a fifth joint rotationally connected to the fourth joint and the sixth joint, respectively.

In one embodiment, a rotation axis of the first joint is parallel to a height direction of the trolley rack, and perpendicular to the rotation axis of the second joint.

In one embodiment, a rotation axis of the fourth joint, a rotation axis of the fifth joint and a rotation axis of the sixth joint are perpendicular to each other.

In one embodiment, the trolley rack includes a base and a post fixedly provided on the base, and the mechanical arm is provided on the post.

In one embodiment, an adapter flange is provided on a side surface of the post, and the mechanical arm is fixedly connected to the adapter flange.

In one embodiment, a top end of the post is provided with a mechanical interface, and the mechanical arm is fixedly connected to the mechanical interface.

In one embodiment, a wire pipe is provided on the first joint at a position connected to the trolley rack, and an axial direction of the wire pipe is perpendicular to an axial direction of the first joint and a height direction of the post, respectively.

In one embodiment, the bottom of the base is provided with two directional casters and two universal casters having a braking function, respectively.

Compared with the prior art, the advantages of the present disclosure lie in that: as the mechanical arm has at least six degrees of freedom, the mechanical arm can completely simulate the movement range of the human arm, and has the same flexibility as the human arm, so as to accurately position the lesion position which actually needs to be operated without requiring a doctor to assist in operation.

BRIEF DESCRIPTION OF THE DRAWINGS

The present disclosure will be described in more detail below on the basis of embodiments and with reference to the accompanying drawings.

DETAILED DESCRIPTION

The present disclosure will be further described below in combination with the accompanying drawings.

Figure 1:
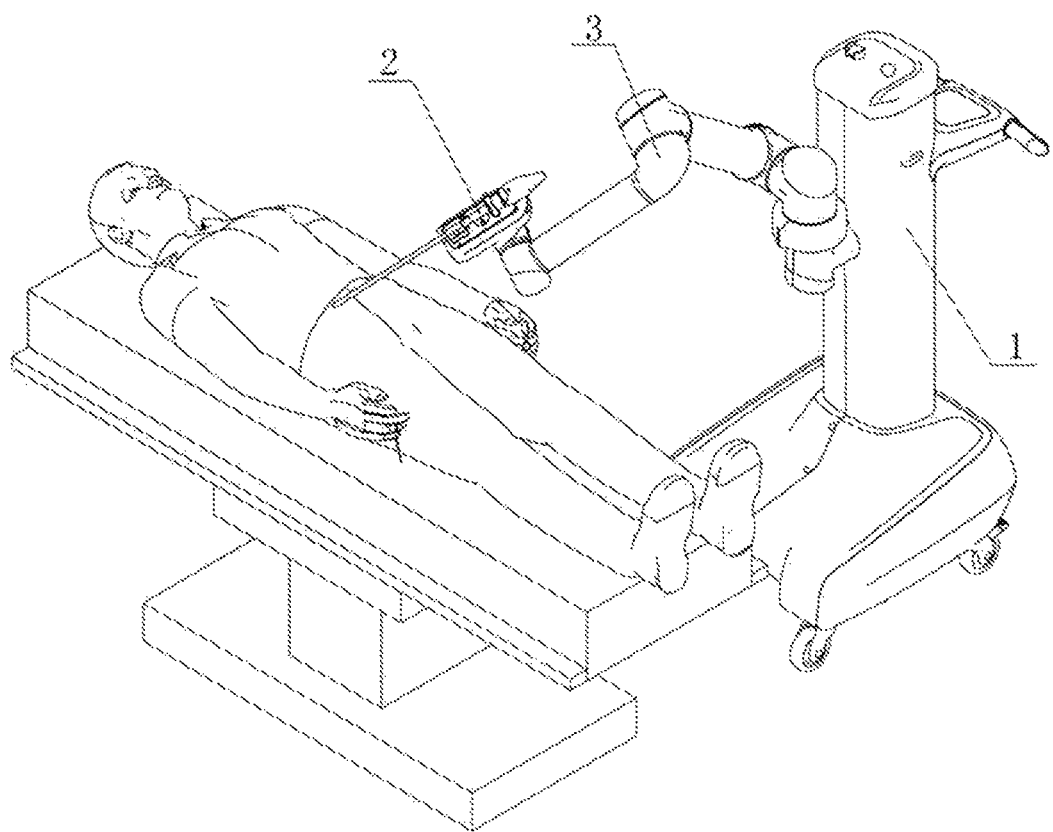
FIG. 1 is a schematic view of operation of a laparoscope-holding robot system for laparoscopic surgery in one embodiment of the present disclosure.

As shown in FIG. 1, the present disclosure provides a laparoscope-holding robot system for laparoscopic surgery, including a trolley rack 1, a surgical tool 2 and a mechanical arm 3 provided on the trolley rack 1. In the laparoscopic surgery, the surgical tool 2 is an endoscope, and of course, the surgical tool 2 also may be other instruments required in minimally invasive surgeries.

The surgical tool 2 is fixed at a front end of the mechanical arm 3, wherein the mechanical arm 3 has at least six degrees of freedom. For example, the mechanical arm 3 may have six degrees of freedom of rotation and more than one degree of translational freedom.

According to a first aspect of the present disclosure, the six degrees of freedom of rotation of the mechanical arm 3 are realized in a following manner.

The mechanical arm 3 includes a terminal joint and an intermediate joint respectively connected to a first connecting arm 37 and a second connecting arm 38, and the terminal joint includes a first joint 31 connected to the trolley rack 1 and a sixth joint 36 connected to a mounting seat 21 of the surgical tool 2.

Further, the intermediate joint includes a second joint 32 rotationally connected to the first joint 31, a third joint 33 connecting the first connecting arm 37 and the second connecting arm 38, a fourth joint 34 rotationally connected to the second connecting arm 38 and a fifth joint 35 rotationally connected to the fourth joint 34 and the sixth joint 36, respectively. That is, two ends of the first connecting arm 37 are respectively connected to the second joint 32 and the third joint 33, and relative movement between the first connecting arm 37 and the second connecting arm 38 is realized by means of the third joint 33.

Figure 2:
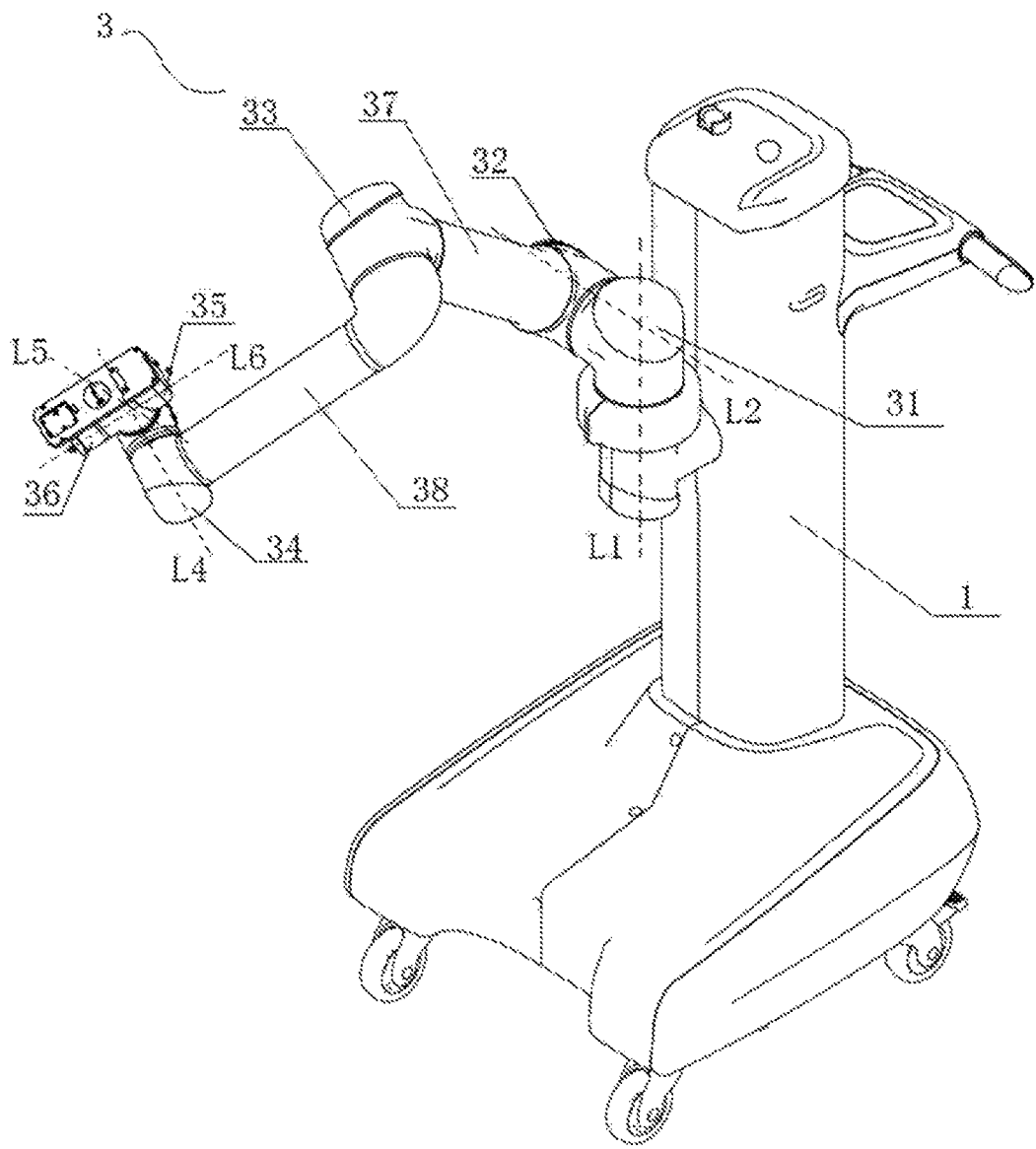
FIG. 2 is a schematic perspective structural view of the laparoscope-holding robot system for laparoscopic surgery in one embodiment of the present disclosure (no surgical tool is shown in the drawing)
Figure 7:
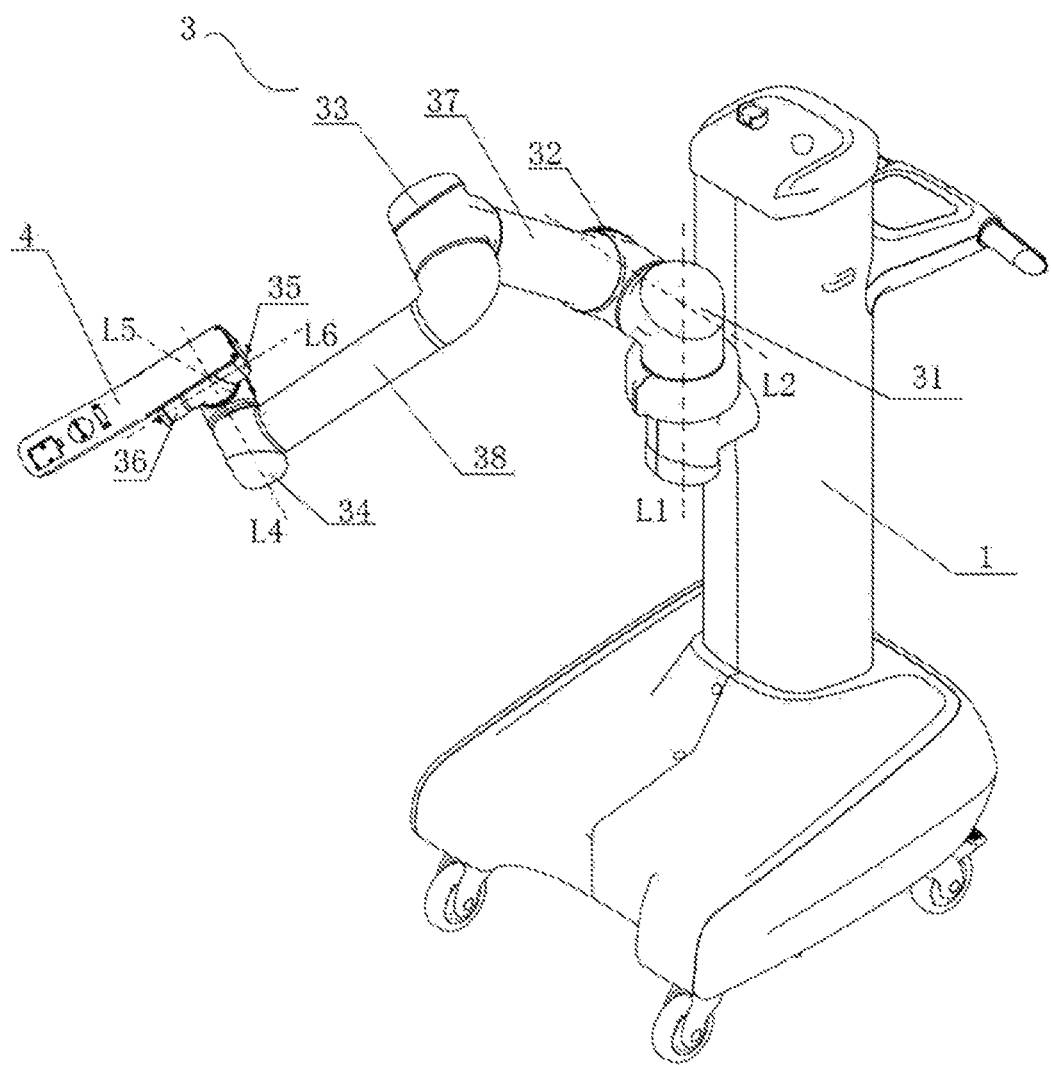
FIG. 7 is a schematic perspective structural view of the laparoscope-holding robot system for laparoscopic surgery in another embodiment of the present disclosure (no surgical tool is shown in the drawing)

As shown in FIG. 2 (or FIG. 7), a rotation axis L1 of the first joint 31 is parallel to a height direction of the trolley rack 1, and perpendicular to a rotation axis L2 of the second joint 2. A rotation axis L4 of the fourth joint 34, a rotation axis L5 of the fifth joint 35 and a rotation axis L6 of the sixth joint 36 are perpendicular to each other. Through the rotation of the six joints above, the six degrees of freedom of rotation of the mechanical arm 3 can be realized, so that the action of the mechanical arm 3 can completely simulate the movement of the human arm, so as to accurately position the lesion position which actually needs to be operated without requiring a doctor to assist in operation, so that the doctor's sight overlaps the lesion position that needs to be operated, avoiding increased operation risk caused by inconsistency of hands and eyes of the doctor.

Besides, each of the six joints above may be provided with a joint sensor, so as to measure an angle of rotation of each joint, thereby obtaining current posture information of the endoscope; moreover, all of the six joints above may be driven by a motor.

Further, each of the above joints is an execution unit of action, and the respective execution units are connected in series, so that the respective joints have relatively good isotropy therebetween, without accumulated error, thus the whole machine of robot is enabled to have relatively high precision, and has the technical features such as good dynamic response.

Figure 4:
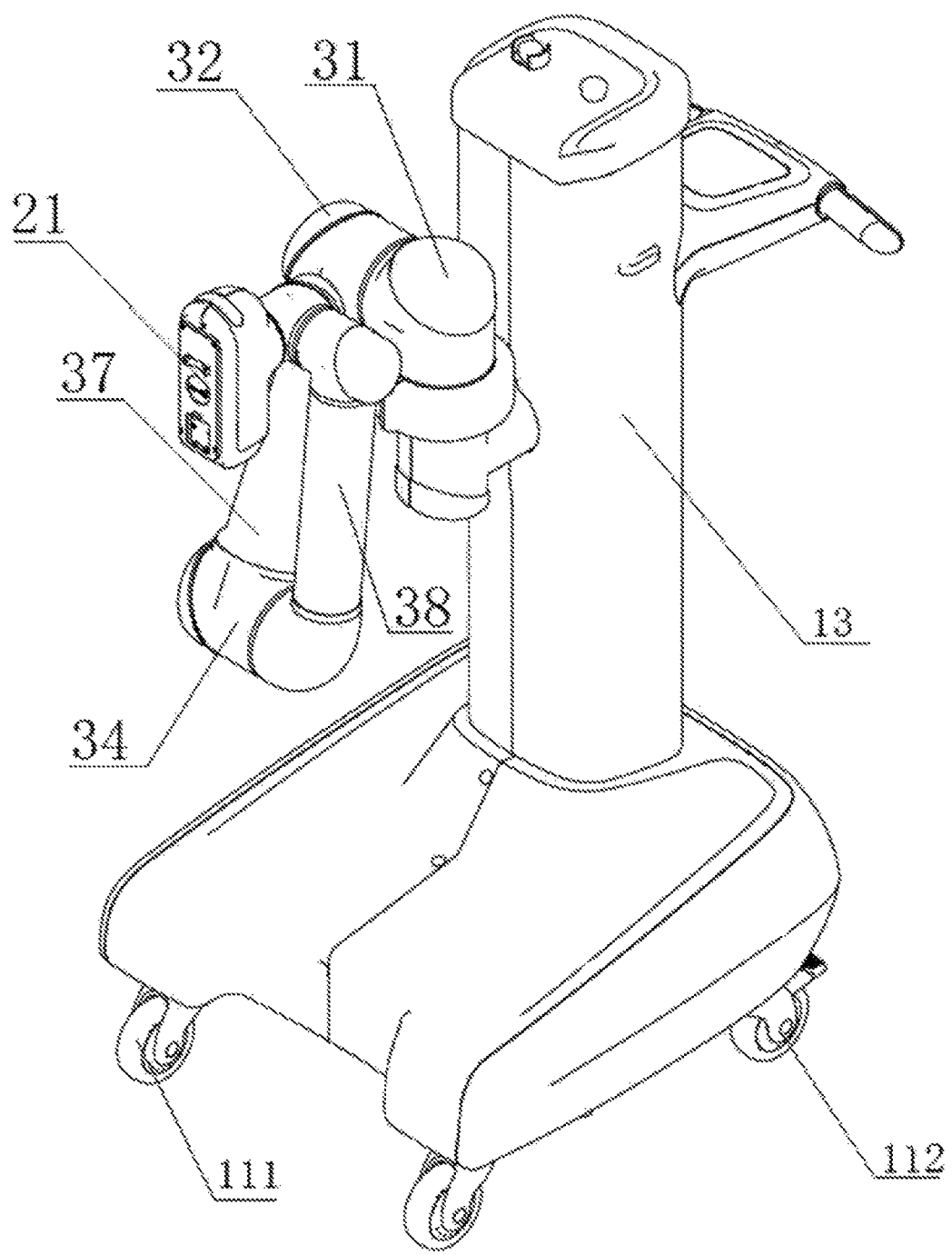
FIG. 4 is a schematic view of a mechanical limit position of the mechanical arm shown in FIG. 1 (no surgical tool is shown in the drawing)

When the second connecting arm 38 rotates with an axis of the third joint 33 as a rotation axis, a maximum rotation angle is 360°. As shown in FIG. 4, it shows one mechanical limit position of the second connecting arm 38.

When the first connecting arm 37 rotates with an axis of the second joint 32 as a rotation axis, a maximum rotation angle is 180°.

In one embodiment of the present disclosure, the number of the above mechanical arms 3 may be two or more, the plurality of mechanical arms 3 may be fixed on different side portions of the trolley rack 1, and terminals of the mechanical arms 3 may be mounted with different surgical tools 2, so as to satisfy requirements of complex surgeries.

Figure 5:
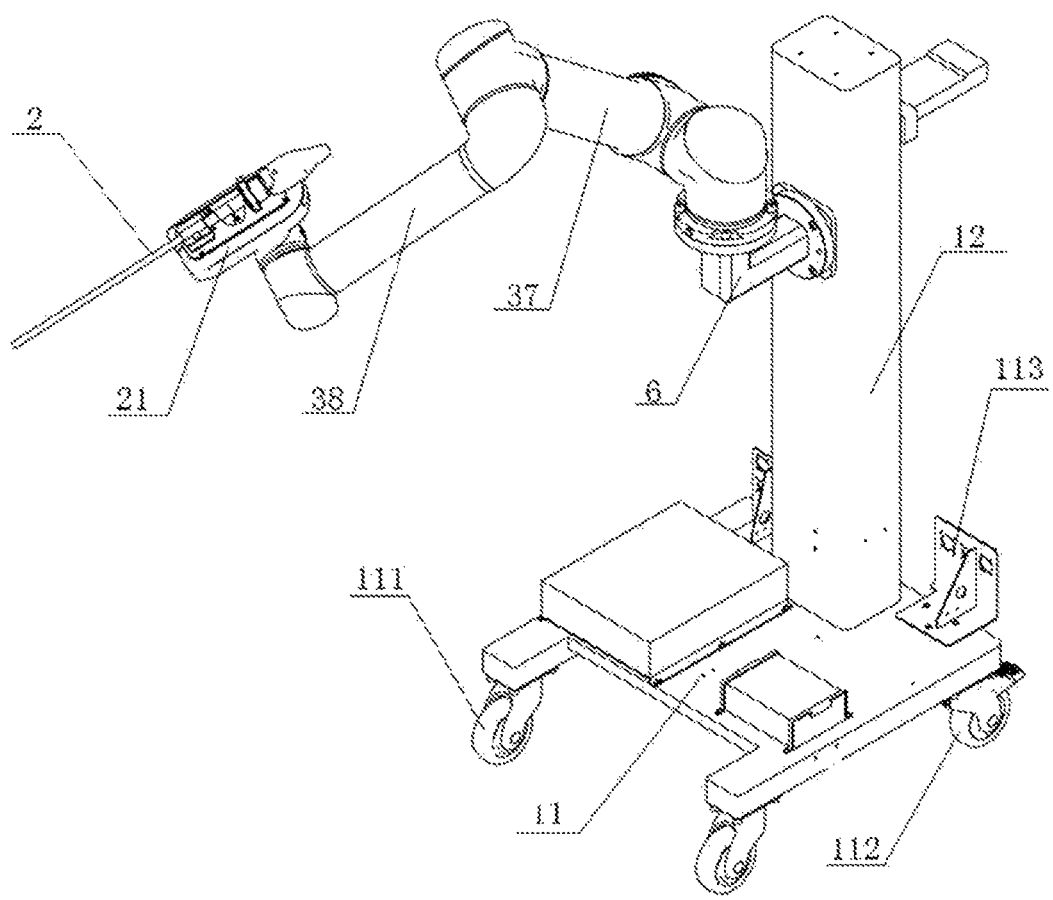
FIG. 5 is a schematic perspective structural view of a base shown in FIG. 1.
Figure 8:
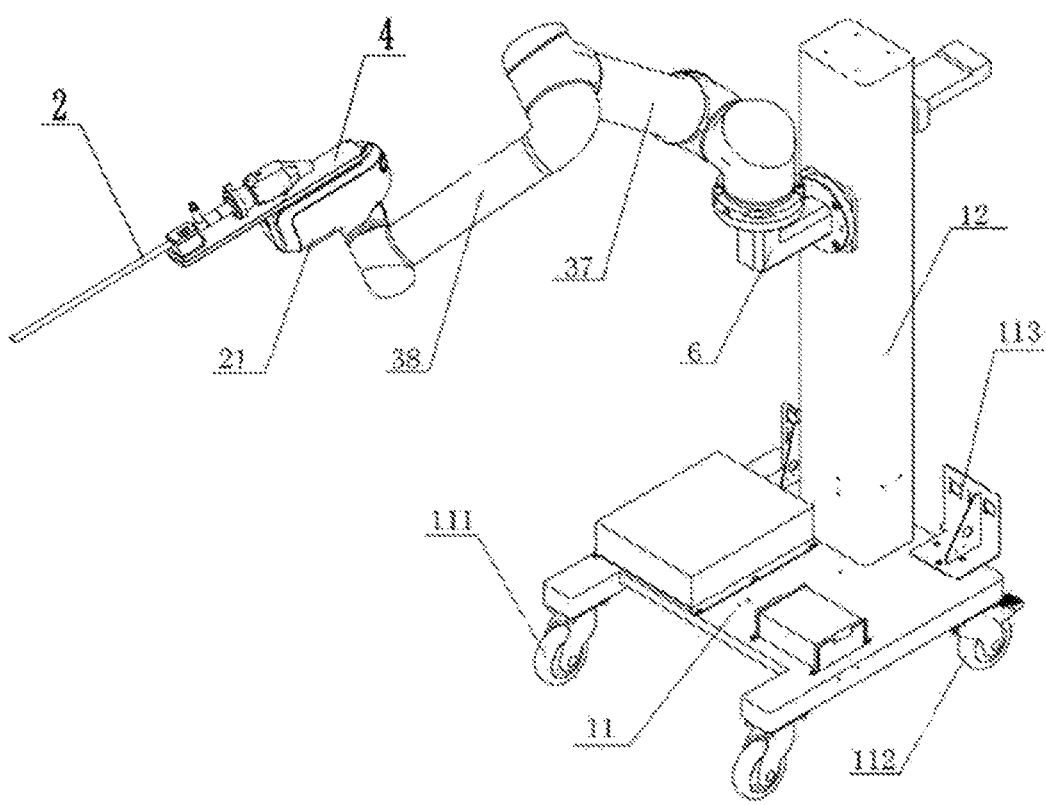
FIG. 8 is a schematic perspective structural view of the base shown in FIG. 6.

As shown in FIG. 5 (or FIG. 8), the trolley rack 1 includes a base 11 and a post 12 fixedly provided on the base 11, and the mechanical arm 3 is provided on the post 12. The base 11 and the post 12 are both provided inside the housing 13, and the housing 13 not only integrate control components and mechanical components, but also can give a good appearance.

In the above, the base 11 is provided with a connecting plate 113, and the connecting plate 113 has one end fixedly connected to a bottom surface of the base 11, and the other end fixedly connected to the housing 13. Specifically, the connecting plate 113 is configured in an L shape, and a cable outlet is provided on the connecting plate 113 at a position connected to the housing. Besides, in order to enhance the strength of the connecting plate 113, reinforcing ribs are provided on the connecting plate 113.

In one embodiment of the present disclosure, the mechanical arm 3 is provided on a side surface of the post 12.

Optionally, an adapter flange 6 is provided on a side surface of the post 12, and the mechanical arm 3 is fixedly connected to the adapter flange 6. In the above, the adapter flange 6 is configured in an L shape, and has one end fixedly connected to a side surface of the post 12, and the other end fixedly connected to a bottom end of the first joint 31.

According to a second aspect of the present disclosure, one degree of translational freedom of the mechanical arm 3 is realized in a following manner.

The post 12 is provided with a sliding sleeve, and the mechanical arm 3 is fixedly connected to the sliding sleeve. The sliding sleeve can slide on the post 12, so as to realize one degree of translational freedom of the mechanical arm 3.

In one embodiment of the present disclosure, the mechanical arm 3 is provided on a top end of the post 12. In the above, the top end of the post 12 is provided with a mechanical interface, and the mechanical arm 3 is fixedly connected to the mechanical interface.

When the mechanical arm 3 is provided on the side surface of the post 12, and an upper end of the housing 13 is provided with an indicator light and/or a control button, so as to facilitate control over the mechanical arm 3.

Besides, the housing 13 further may be provided with a support plate, which may be used as a support platform, on the other side opposite to the mechanical arm 3.

Figure 3:
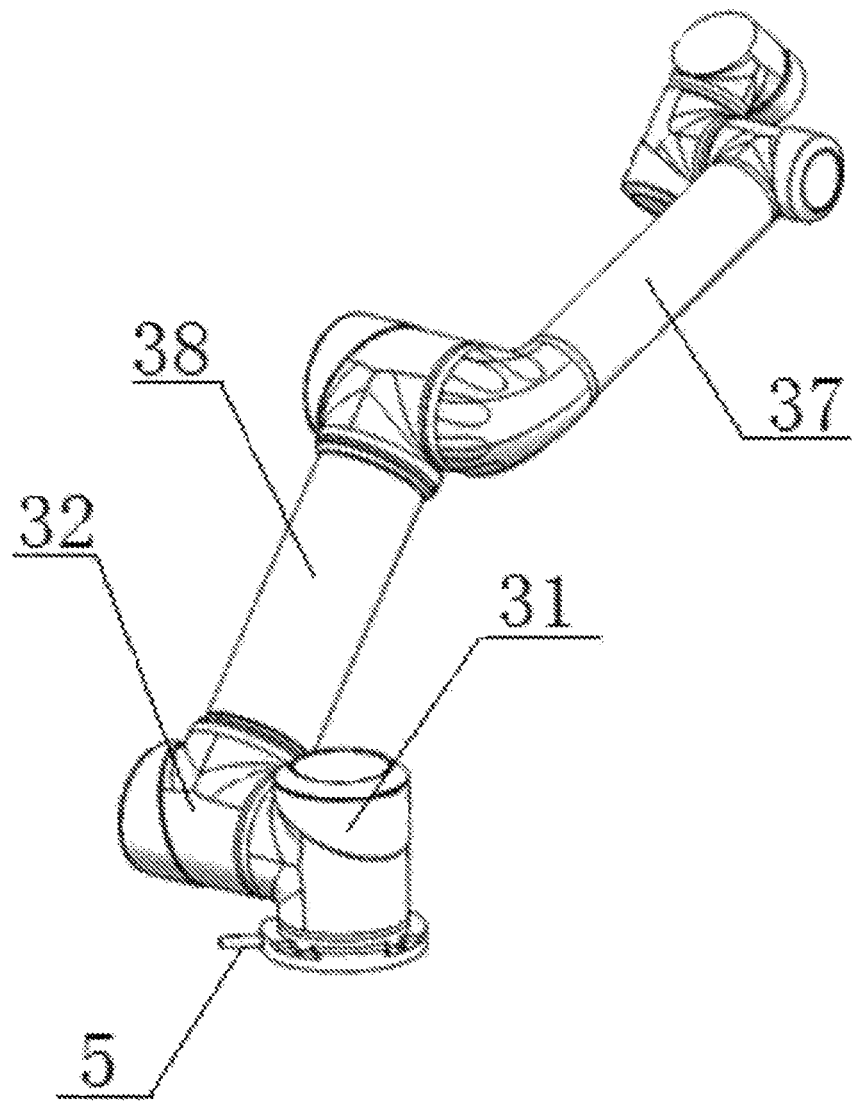
FIG. 3 is a schematic structural view of a mechanical arm shown in FIG. 2.

As shown in FIG. 3, the first joint 31 is provided with a wire pipe 5 at a position connected to the trolley rack 1, and an axial direction of the wire pipe 5 is perpendicular to an axial direction of the first joint 31 and a height direction of the post 12, respectively. Similarly, the six joint 36 is provided with a wire pipe at a position connected to the mounting base 21, so as to protect the wire led out from the joint.

The bottom of the base 11 is provided with two directional casters 111 and two universal casters 112 having a braking function, respectively. Each universal caster 112 may be provided with a brake device such as brake block, so as to realize the function of designated parking.

Besides, in order to facilitate operation, the directional casters 111 are provided at a front side of the post 12, and the universal casters 112 are provided at a rear side of the post 12.

In addition, it should be noted that an RCM point of the laparoscope-holding robot system for laparoscopic surgery in the present disclosure is ensured by the algorithm of control components.

In one embodiment of the present disclosure, the surgical tool 2 (i.e., endoscope) is connected to the sixth joint 36 through the mounting base 21. In the above, the mounting base 21 is provided with a baseboard, the baseboard is provided with a quick-release device, and quick disassembling and mounting between the surgical tool and the mechanical arm 3 can be realized by the quick-release device.

Figure 6:
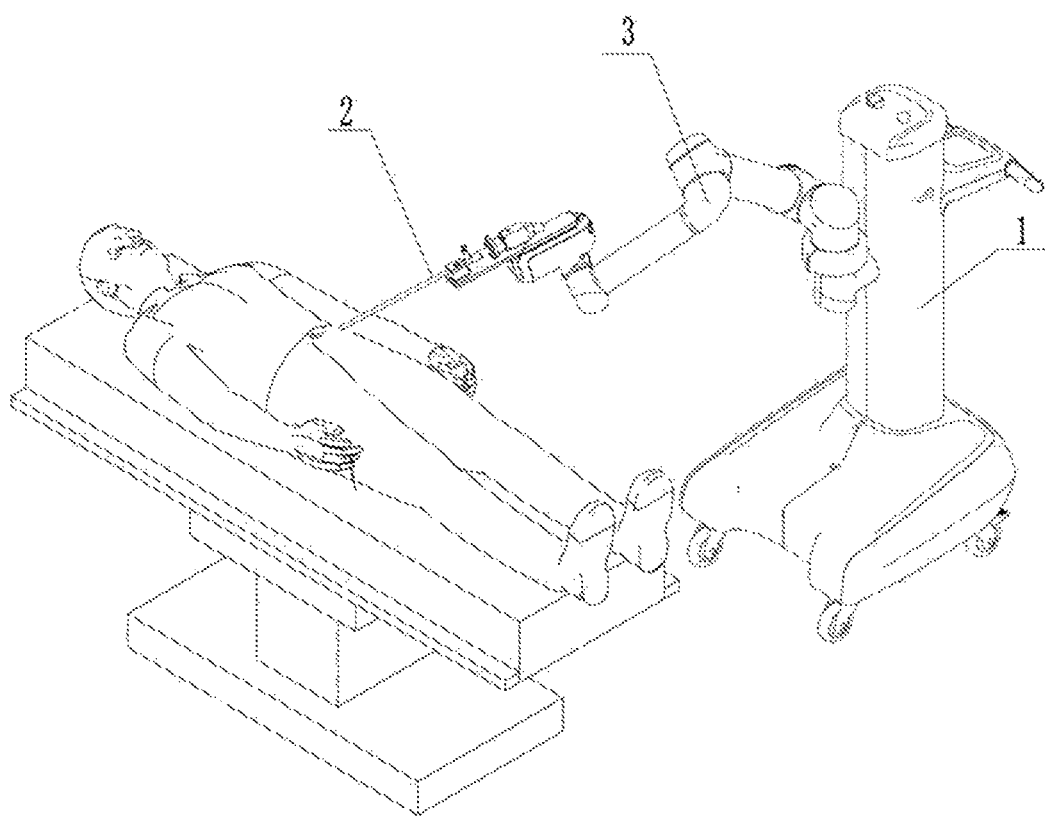
FIG. 6 is a schematic view of operation of the laparoscope-holding robot system for laparoscopic surgery in another embodiment of the present disclosure.

On the basis of the above embodiment, in another embodiment of the present disclosure, as shown in FIG. 6, the present disclosure provides a laparoscope-holding robot system for laparoscopic surgery, including a trolley rack 1, a surgical tool 2 and a mechanical arm 3 provided on the trolley rack 1. A front end of the mechanical arm 3 is provided with an extension plate 4 having the quick-release device, and the surgical tool 2 is fixed on the extension plate 4 by the quick-release device. A specific fixing manner will be described in detail below.

Figure 10:
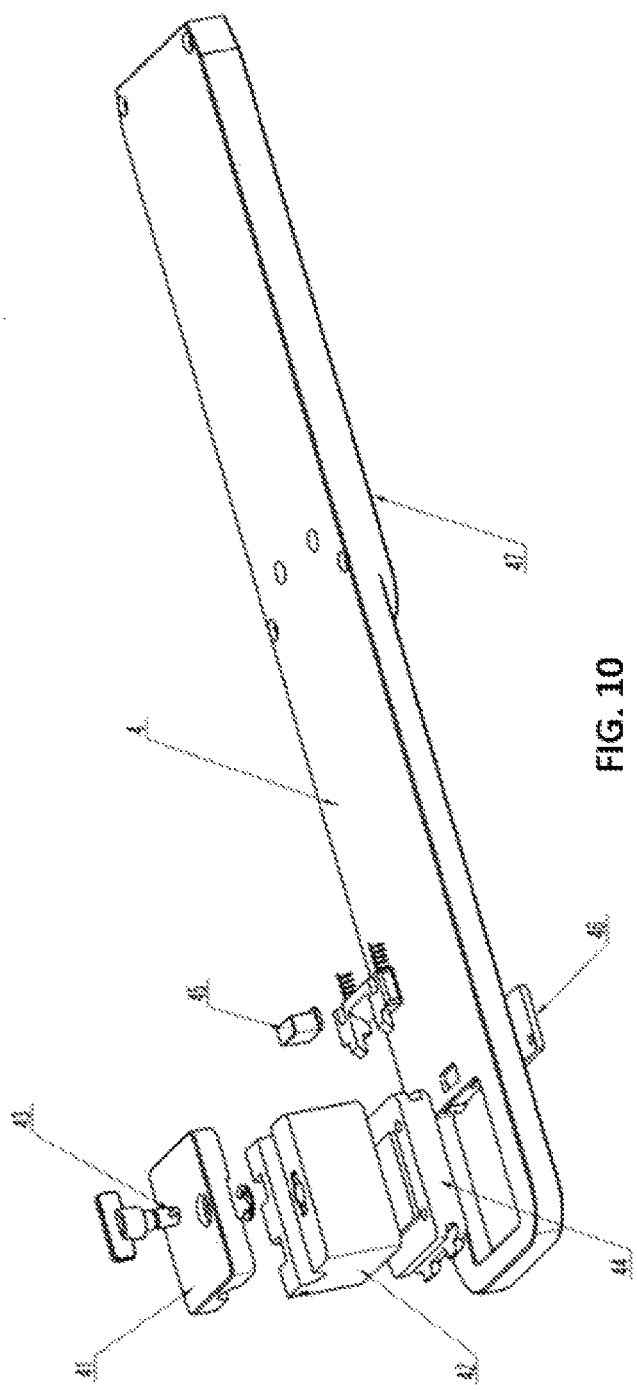
FIG. 10 is an explosive view of an extension plate shown in FIG. 6.

As shown in FIG. 10, a bottom end of the extension plate 4 is provided with a mounting portion 47, the mounting portion 47 is provided on the mounting base 21, the extension plate 4 has the quick-release device, and quick disassembling and mounting between the surgical tool and the mechanical arm 3 can be realized by the quick-release device.

Figure 9:
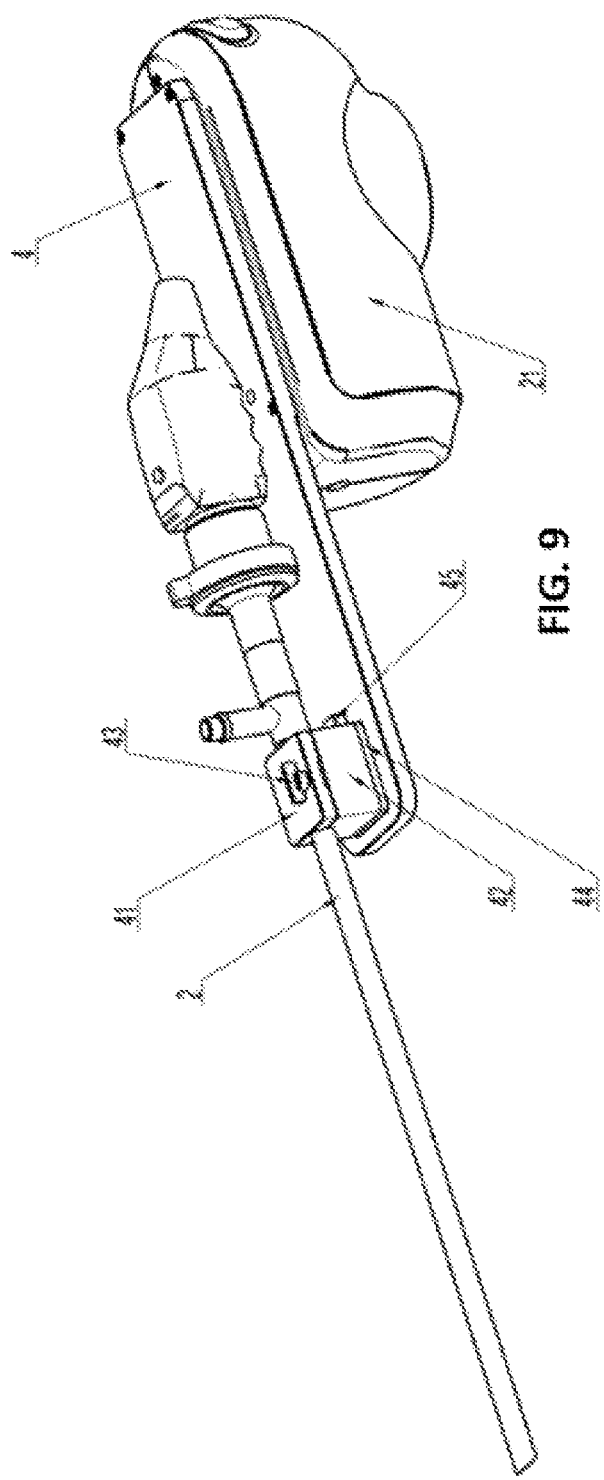
FIG. 9 is a schematic perspective structural view of an extension plate shown in FIG. 6.

Specifically, as shown in FIG. 9 and FIG. 10, the extension plate is provided with an upper connecting block 41 and a lower connecting block 42, the upper connecting block 41 and the lower connecting block 42 are hinged, the upper connecting block 41 and the lower connecting block 42 are each provided with a semicircular groove, and when the upper connecting block 41 and the lower connecting block 42 are put together, the two semicircular grooves form a mounting hole, the front end of the endoscope extends into the mounting hole, and a rear end of the endoscope is in contact with the extension plate 4, so that two supporting points are formed on the extension plate 4, so as to stably support the endoscope.

When the endoscope is provided in the mounting hole, the upper connecting block 41 and the lower connecting block 42 are locked by a first quick-release device, i.e. a locking pin shaft 43, so as to fix the endoscope in the mounting hole. Specifically, the locking pin shaft 43 can rotate in the upper connecting block 41 and the lower connecting block 42, and be engaged with a boss on the bottom of the lower connecting block 42, to lock the upper connecting block 41 and the lower connecting block 42.

Besides, the lower connecting block 42 is provided with an adapter block 44 at its bottom, and the adapter block 44 and the extension plate 4 are fixed by a second quick-release device, i.e. an elastic fixture block. Specifically, the elastic fixture block is provided inside the extension plate 4, the extension plate 4 is provided with a cover plate 46 at the bottom, and the elastic fixture block and the extension plate 4 can generate relative movement through a compression spring. An end of the elastic fixture block is inserted into the adapter block 44, and is snap-fitted with the adapter block 44, so that the adapter block 44 is fixed on the extension plate 4. When disassembling is needed, the lock button 45 is pressed down, then the elastic fixture block moves towards a direction away from the adapter block 44, so that no snap-fit relationship is generated any more between the elastic fixture block and the adapter block 44, then the adapter block 44 can be taken away from the extension plate 4, thus achieving the purpose of quick disassembling.

Although the present disclosure has been described with reference to preferred embodiments, various improvements can be made thereto and components therein may be replaced by equivalents, without departing from the scope of the present disclosure. In particular, various technical features mentioned in various embodiments may be combined in any manner as long as there is no structural conflict. The present disclosure is not restricted to specific embodiments disclosed herein, but covers all technical solutions falling within the scope of the claims.

What is claimed is:

1. A laparoscope-holding robot system for laparoscopic surgery, comprising:
  a trolley rack, wherein the trolley rack comprises a base, a stationary post immovably fixed to the base, and a sliding sleeve on the post; and a mechanical arm on the trolley rack, wherein the mechanical arm is connected at one end thereof to the sliding sleeve, wherein the mechanical arm has at least six degrees of rotational freedom and at least one degree of translational freedom, and wherein one degree of translational freedom is provided to the mechanical arm by the sliding sleeve sliding on the post, wherein the mechanical arm comprises a terminal joint and an intermediate joint respectively connected to a first connecting arm and a second connecting arm, and the terminal joint comprises a first joint connected to the trolley rack and a sixth joint connected to a mounting seat of a surgical tool, wherein the intermediate joint comprises a second joint rotationally connected to the first joint, a third joint connecting the first connecting arm and the second connecting arm, a fourth joint rotationally connected to the second connecting arm and a fifth joint respectively rotationally connected to the fourth joint and the sixth joint, wherein a top end of the post is provided with a mechanical interface, and the mechanical arm is fixedly connected to the mechanical interface.

2. The laparoscope-holding robot system for laparoscopic surgery according to claim 1, wherein when the second connecting arm is rotated with an axis of the third joint as a rotation axis, a maximum rotation angle is 360°.

3. The laparoscope-holding robot system for laparoscopic surgery according to claim 1, wherein when the first connecting arm is rotated with an axis of the second joint as a rotation axis, a maximum rotation angle is 180°.

4. The laparoscope-holding robot system for laparoscopic surgery according to claim 2, wherein when the first connecting arm is rotated with an axis of the second joint as a rotation axis, a maximum rotation angle is 180°.

5. The laparoscope-holding robot system for laparoscopic surgery according to claim 1, wherein the first joint is provided with a wire pipe at a position connected to the trolley rack, and an axial direction of the wire pipe is perpendicular to an axial direction of the first joint and a height direction of the post, respectively.

6. The laparoscope-holding robot system for laparoscopic surgery according to claim 1, wherein a bottom of the base is provided with two directional casters and two universal casters having a braking function, respectively.

7. A laparoscope-holding robot system for laparoscopic surgery, comprising:
a trolley rack,
wherein the trolley rack comprises a base and a single stationary post immovably fixed to the base; and
a mechanical arm on the post,
wherein the mechanical arm includes an extension plate having a quick-release device configured to receive a surgical tool,
wherein the mechanical arm has at least six degrees of freedom comprising rotational freedom, translational freedom, or a combination thereof,
wherein the mechanical arm comprises a first joint having a rotational axis and a second joint having a rotational axis;
wherein the rotational axis of the first joint is offset from and parallel to a height direction of the post,
wherein the rotational axis of the first joint is perpendicular to the rotational axis of the second joint, and wherein a top end of the post is provided with a mechanical interface, and the mechanical arm is fixedly connected to the mechanical interface.

8. The laparoscope-holding robot system for laparoscopic surgery according to claim 7, wherein the mechanical arm comprises a terminal joint and an intermediate joint respectively connected to a first connecting arm and a second connecting arm, and the terminal joint comprises the first joint connected to the trolley rack and a sixth joint connected to a mounting seat of the surgical tool.

9. The laparoscope-holding robot system for laparoscopic surgery according to claim 8, wherein the intermediate joint comprises a second joint rotationally connected to the first joint, a third joint connecting the first connecting arm and the second connecting arm, a fourth joint rotationally connected to the second connecting arm and a fifth joint respectively rotationally connected to the fourth joint and the sixth joint.

10. The laparoscope-holding robot system for laparoscopic surgery according to claim 9, wherein a rotation axis of the fourth joint, a rotation axis of the fifth joint and a rotation axis of the sixth joint are perpendicular to each other.

11. The laparoscope-holding robot system for laparoscopic surgery according to claim 7, wherein a rotation axis of the fourth joint, a rotation axis of the fifth joint and a rotation axis of the sixth joint are perpendicular to each other.

12. The laparoscope-holding robot system for laparoscopic surgery according to claim 7, wherein the first joint is provided with a wire pipe at a position connected to the trolley rack, and an axial direction of the wire pipe is perpendicular to an axial direction of the first joint and a height direction of the post, respectively.

13. The laparoscope-holding robot system for laparoscopic surgery according to claim 7, wherein a bottom of the base is provided with two directional casters and two universal casters having a braking function, respectively.

14. The laparoscope-holding robot system for laparoscopic surgery according to claim 8, further comprising:
a mounting base coupled to the sixth joint, the mounting base having a top surface,
wherein the extension plate has a bottom surface, the bottom surface having a mounting portion coupled to the top surface of the mounting base.

15. The laparoscope-holding robot system for laparoscopic surgery according to claim 1, wherein the first joint is connected to the sliding sleeve.

16. The laparoscope-holding robot system for laparoscopic surgery according to claim 15, wherein the first joint is connected to the sliding sleeve by an adapter flange.

17. A laparoscope-holding robot system for laparoscopic surgery, comprising:
a trolley rack,
wherein the trolley rack comprises a base and a single stationary post immovably fixed to the base;
a mechanical arm on the post,
wherein the mechanical arm includes an extension plate having a quick-release device configured to receive a surgical tool,
wherein the mechanical arm has at least six degrees of freedom comprising rotational freedom, translational freedom, or a combination thereof,
wherein the mechanical arm comprises a first joint having a rotational axis and a second joint having a rotational axis;

wherein the rotational axis of the first joint is offset from and parallel to a height direction of the post, wherein the rotational axis of the first joint is perpendicular to the rotational axis of the second joint, and wherein the mechanical arm comprises a terminal joint and an intermediate joint respectively connected to a first connecting arm and a second connecting arm, and the terminal joint comprises the first joint connected to the trolley rack and a sixth joint connected to a mounting seat of the surgical tool; and a mounting base coupled to the sixth joint, the mounting base having a top surface, wherein the extension plate has a bottom surface, the bottom surface having a mounting portion coupled to the top surface of the mounting base.

18. The laparoscope-holding robot system for laparoscopic surgery according to claim 17, wherein the intermediate joint comprises a second joint rotationally connected to the first joint, a third joint connecting the first connecting arm and the second connecting arm, a fourth joint rotationally connected to the second connecting arm and a fifth joint respectively rotationally connected to the fourth joint and the sixth joint.

19. The laparoscope-holding robot system for laparoscopic surgery according to claim 18, wherein a rotation axis of the fourth joint, a rotation axis of the fifth joint and a rotation axis of the sixth joint are perpendicular to each other.

20. The laparoscope-holding robot system for laparoscopic surgery according to claim 17, wherein a rotation axis of the fourth joint, a rotation axis of the fifth joint and a rotation axis of the sixth joint are perpendicular to each other.

21. The laparoscope-holding robot system for laparoscopic surgery according to claim 17, wherein the first joint is provided with a wire pipe at a position connected to the trolley rack, and an axial direction of the wire pipe is perpendicular to an axial direction of the first joint and a height direction of the post, respectively.

22. The laparoscope-holding robot system for laparoscopic surgery according to claim 17, wherein a bottom of the base is provided with two directional casters and two universal casters having a braking function, respectively.

* * * * *